(12) United States Patent
Yoon et al.

(10) Patent No.: US 9,664,630 B2
(45) Date of Patent: May 30, 2017

(54) HUMIDITY SENSOR, HUMIDITY SENSING METHOD AND TRANSISTOR THEREFOR

(75) Inventors: Jun Bo Yoon, Daejeon (KR); Hyun Ho Yang, Daejeon (KR); Seok Ho Song, Daejeon (KR)

(73) Assignee: Korea Advanced Institute of Science & Technology, Daejeon (KR)

( * ) Notice: Subject to any disclaimer, the term of this patent is extended or adjusted under 35 U.S.C. 154(b) by 708 days.

(21) Appl. No.: 14/110,059

(22) PCT Filed: Feb. 15, 2012

(86) PCT No.: PCT/KR2012/001138
§ 371 (c)(1),
(2), (4) Date: Nov. 1, 2013

(87) PCT Pub. No.: WO2012/138054
PCT Pub. Date: Oct. 11, 2012

(65) Prior Publication Data
US 2014/0298904 A1    Oct. 9, 2014

(30) Foreign Application Priority Data

Apr. 7, 2011  (KR) .................. 10-2011-0032135

(51) Int. Cl.
G01N 27/04 (2006.01)
G01N 27/414 (2006.01)

(52) U.S. Cl.
CPC ....... *G01N 27/048* (2013.01); *G01N 27/4141* (2013.01)

(58) Field of Classification Search
CPC ............. G01N 27/048; G01N 27/4141; G01N 27/223; G01N 27/4148

USPC .......... 73/73, 335.05, 335.02, 335.04, 31.06, 73/29.01; 324/694, 664, 691, 71.5
See application file for complete search history.

(56) References Cited

U.S. PATENT DOCUMENTS

| | | | | |
|---|---|---|---|---|
| 4,158,807 A | * | 6/1979 | Senturia | H01L 29/42312 257/253 |
| 5,004,700 A | * | 4/1991 | Webb | G01N 27/4141 257/414 |
| 8,325,460 B2 | * | 12/2012 | Park | G01N 27/223 361/278 |
| 2004/0008471 A1 | * | 1/2004 | Davis | G01N 27/225 361/306.3 |

(Continued)

FOREIGN PATENT DOCUMENTS

| | | |
|---|---|---|
| JP | 08-082612 A | 3/1996 |
| JP | 2001-194332 A | 7/2001 |
| KR | 10-1995-0002080 B1 | 3/1995 |

OTHER PUBLICATIONS

International Search Report for PCT/KR2012/001138; mailed Sep. 28, 2012; 2 pages.

(Continued)

*Primary Examiner* — Hezron E Williams
*Assistant Examiner* — Marrit Eyassu
(74) *Attorney, Agent, or Firm* — Foley & Lardner LLP

(57) ABSTRACT

Disclosed is a humidity sensor including: a conductive material in which electric charges are charged; a charger which charges the electric charges in the conductive material; and a measurer which measures a change amount of the electric charges charged in the conductive material.

9 Claims, 5 Drawing Sheets

(56) References Cited

U.S. PATENT DOCUMENTS

| | | | |
|---|---|---|---|
| 2005/0230271 A1* | 10/2005 | Levon | G01N 27/4148 205/789 |
| 2006/0267202 A1* | 11/2006 | Matsuzaki | H01L 23/5225 257/758 |
| 2007/0105285 A1* | 5/2007 | Kusumoto | B82Y 10/00 438/151 |

OTHER PUBLICATIONS

Lee, Sung-Pil; "A Design of FET type Multi-functional Temperature Humidity Sensors"; Theses Collection vol. 14, No. 2, 1997, pp. 229-235; The Research Institute of Engineering Technology, Kyungnam University, Masan Korea 631-701.

Office Action in KR application No. 10-2011-0032135; May 30, 2013; 3 pages.

Office Action in KR application No. 10-2011-0032135; Oct. 30, 2012; 3 pages.

\* cited by examiner

HUMIDITY SENSOR, HUMIDITY SENSING METHOD AND TRANSISTOR THEREFOR

This application is the National Phase of PCT/KR2012/001138, filed Feb. 15, 2012, which claims priority to Korean Application No. 10-2011-0032135, filed Apr. 7, 2011, the disclosures of which are hereby incorporated by reference in their entirety.

TECHNICAL FIELD

The present invention relates to a humidity sensor, a humidity sensing method and a transistor for the same.

BACKGROUND ART

A humidity sensor may be applied to a variety of industries in the form of being used individually or together with sensors that obtain other kinds of information. The humidity sensor may be applied to logistics services, transport services and traffic network, etc., thereby enhancing services related thereto. Also, the humidity sensor may be applied to history management, production management, plant management and environment network construction of agriculture, fisheries, livestock industry, distribution industry and manufacturing industry and the like, and may be also applied to smart home, office network and building control and the like with the intention of making a residential space pleasant. The humidity sensor may be also used to deal with other hazardous industry environment.

For the purpose of incorporating the humidity sensor with the above-mentioned various services, research is being devoted to higher sensibility, miniaturization, a lower price and reliability. In terms of the structure of the humidity sensor, the humidity sensor is recently evolving from a ceramic sintering or thick film structure to a micro sensor structure that chiefly uses a micro-electro-mechanical system technology to which a semiconductor process technology has been applied.

A humidity sensor's measurement method using a humidity sensing film is now the most widely used. The measurement method is to measure the electrical characteristics at a point of time when moisture is absorbed in or desorbed from the humidity sensing film composed generally of organic matter like polymer, etc., or inorganic matter like ceramic, etc. The measurement method is relatively simple. For example, the humidity is detected by the capacitance change or resistance change caused by the moisture absorption of the humidity sensing film. The humidity sensor using the above-mentioned humidity sensing film commonly uses a structure provided with only the humidity sensing film and sensing electrode.

However, regarding the conventional humidity sensor using the above-mentioned humidity sensing film, in a case where defects occur in manufacturing the humidity sensing film, a signal may be distorted due to the influence of a parasitic capacitance. Moreover, since the polymer layer should absorb the moisture, the reaction rate is low. Additionally, much time is required for detecting rapid change of the humidity. Also, the polymer is vulnerable to organic solvent like alcohol, etc., and may have a problem in adhering to electrodes. Besides, it is difficult to obtain stable characteristics under high temperature and high humidity conditions.

Therefore, there is a requirement for development of a humidity sensor capable of rapidly and accurately detecting humidity and of being applied to any medium.

DISCLOSURE

Technical Problem

The present invention is provided to overcome the above-mentioned problems of the prior art. The present invention provides a humidity sensor capable of rapidly and accurately detecting humidity and a humidity sensing method. The present invention provides a humidity sensor capable of accurately detecting humidity in any medium and a humidity sensing method. The present invention provides a humidity sensor which is mass-produced, easy to process and has high reliability and high reproductivity, and a humidity sensing method. Also, the present invention provides a transistor for sensing the humidity.

The technical problem to be overcome by the present invention is not limited to the above-mentioned technical problems. Other technical problems not mentioned can be clearly understood from the embodiments of the present invention by a person having ordinary skill in the art.

Technical Solution

A humidity sensor according to an embodiment of the present invention includes: a conductive material in which electric charges are charged; a charger which charges the electric charges in the conductive material; and a measurer which measures a change amount of the electric charges charged in the conductive material.

A humidity sensor according to another embodiment of the present invention includes: a transistor including a source and a drain which are formed on a substrate separately from each other with a channel area placed therebetween, an insulation layer formed on the channel area, a gate formed on the insulation layer, a hydrophobic layer covering the gate, the source and the drain, and a conductive material layer which is connected to the gate through a through-hole formed in the hydrophobic layer and is formed on the hydrophobic layer; and a measurer measuring a change amount of drain current of the transistor.

The humidity sensor according to the embodiment of the present invention may further include a humidity sensing layer which is located between the hydrophobic layer and the conductive material layer and of which surface conductivity changes depending on the humidity.

A humidity sensing method according to an embodiment of the present invention includes: charging electric charges in a conductive material; measuring a change amount the electric charges of the conductive material; and calculating humidity of a medium in contact with the conductive material based on the change amount of the electric charges.

A humidity sensing method according to another embodiment of the present invention includes: charging electric charges in a gate of a transistor, wherein the transistor includes a source and a drain which are formed on a substrate separately from each other with a channel area placed therebetween, an insulation layer formed on the channel area, the gate formed on the insulation layer, a hydrophobic layer covering the gate, the source and the drain, and a conductive material layer which is connected to the gate through a through-hole formed in the hydrophobic layer and is formed on the hydrophobic layer; measuring a change amount of drain current of the transistor; and calculating humidity of a medium in contact with the gate based on the change amount of the drain current.

A transistor for sensing humidity according to the embodiment of the present invention includes: a source and a drain which are formed on a substrate separately from each other with a channel area placed therebetween; an insulation layer formed on the channel area; a gate formed on the insulation layer; a hydrophobic layer covering the gate, the source and the drain; and a conductive material layer which is connected to the gate through a through-hole formed in the hydrophobic layer and is formed on the hydrophobic layer.

The transistor for sensing humidity according to the embodiment of the present invention may further include a humidity sensing layer which is located between the hydrophobic layer and the conductive material layer and of which surface conductivity changes depending on the humidity.

Advantageous Effects

The present invention is able to overcome a hysteresis phenomenon, a slow response speed, a long recovery time, unstable characteristics under high temperature and high humidity conditions, poor contact between the metal and a humidity sensing film, and reliability degradation due to the deterioration of the humidity sensing film when a long time has lapsed, and the like of a conventional humidity sensor detecting humidity by the capacitance change or resistance change caused by the moisture absorption of a humidity sensing film. Also, according to the present invention, all parts of the humidity sensor are made of a material used in the semiconductor process, mass production is allowed. Also, according to the present invention, since the polymer is not used in the manufacture of the humidity sensor, the process becomes easy, and high reliability and reproductivity are obtained. Also, according to the present invention, it is possible to provide a humidity sensor capable of accurately detecting humidity in any medium and a humidity sensing method. Also, according to the present invention, it is possible, as described above, to provide a transistor for sensing the humidity.

MODE FOR INVENTION

Figure 1:
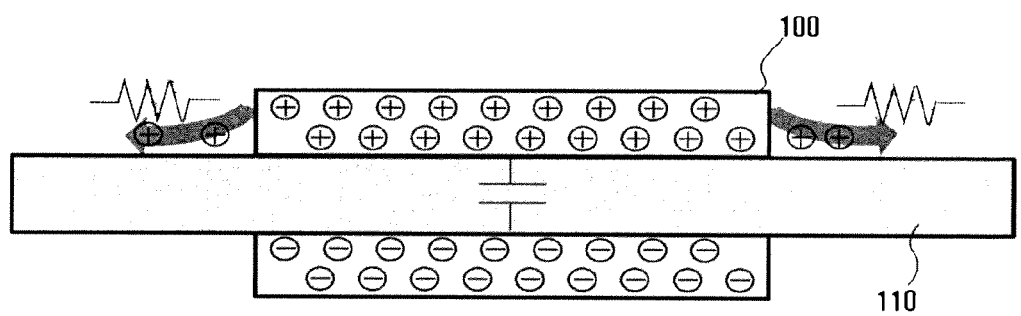
FIG. 1 shows a basic structure of a humidity sensor and a humidity sensing method according to the present invention.

Hereafter, an exemplary embodiment of the present invention will be described in detail with reference to the accompanying drawings. The shapes and sizes and the like of components of the drawings are exaggerated for clarity of the description. It is noted that the same reference numerals are used to denote the same elements throughout the drawings. In the following description of the present invention, the detailed description of known functions and configurations incorporated herein is omitted when it may make the subject matter of the present invention unclear.

Unlike a conventional method, a humidity sensor and a humidity sensing method according to the present invention use an electric charge relaxation effect in which electric charges charged in a conductive material such as metal disappear into the surface of material in contact with the metal with the lapse of time.

FIG. 1 shows a basic structure of a humidity sensor and a humidity sensing method according to the present invention. As shown in FIG. 1, when the electric charges are charged to a conductive material 100 such as the metal, the electric charges within the conductive material 100 is discharged with the lapse of time along the surface of a material 110 in contact with the conductive material 100.

Here, a discharge rate of the electric charges is determined by a surface resistance and a capacitance of the material 110 in contact with the conductive material 100. The surface conductivity of the material 110 is increased with the increase of the surface humidity of the material 110. That is, since the surface resistance of the conductive material 100 among the two factors is reduced with the increase of the humidity, the electric charges charged in the conductive material 100 is rapidly discharged through the surface of the material 110.

Accordingly, the more the humidity of a medium in contact with the material 110 is increased, the more rapidly the electric charges charged in the conductive material 100 is discharged along the surface of the material 110, so that the electric charges within the conductive material 100 are reduced. As mentioned, the phenomenon in which the electric charges charged in the conductive material 100 are discharged is referred to as the electric charge relaxation effect.

The following description shows the electric charge relaxation effect represented by equation 1.

$$Q = Q_0 e^{\frac{-t}{R_S C_S}} \quad \text{equation (1)}$$

Here, $Q_0$ represents an initial (t=0) electric charge amount of the conductive material 100, Q represents a residual electric charge amount of the conductive material 100 after the lapse of time "t", Rs represents a surface resistance of the material 110 in contact with the conductive material, Cs represents the capacitance of the material 110, and RsCs represents the electric charge relaxation constant.

The equation (1) represents that the electric charges charged in the conductive material 100 are exponentially reduced. Here, it can be understood that the denominator (RsCs) of the exponent of the exponential function is determined by the surface resistance and the capacitance of the material 110.

Through the use of the electric charge relaxation effect, the electric charges are charged in the conductive material 100, and the residual electric charge amount in the conductive material 100 after a predetermined time is measured. As a result, a value of the charge relaxation constant (RsCs) can be obtained.

The value of the electric charge relaxation constant (RsCs) is obtained by a function of the surface resistance and the capacitance, and thus can be represented by a function of the surface humidity of the material 110. That is, the disappearance rate of the electric charges charged in the conductive material 100 depends on the humidity.

Therefore, the surface humidity of the material 110 with which the conductive material 100 has contacted can be calculated by measuring the change amount of the electric charges within the conductive material 100 during the predetermined time "t". Here, factors causing the electric charges to disappear from the conductive material 100 may be further considered.

The conductive material 100 of FIG. 1 and a conductive material layer 700 of the following drawings may include a material in which the electric charge can be charged. For example, the conductive material 100 and the conductive material layer 700 may include metal. The metal may be chemically less changed with the lapse of time. For example, the metal may include Au, thereby sensing the humidity with a small error range for a long time.

Figure 2:
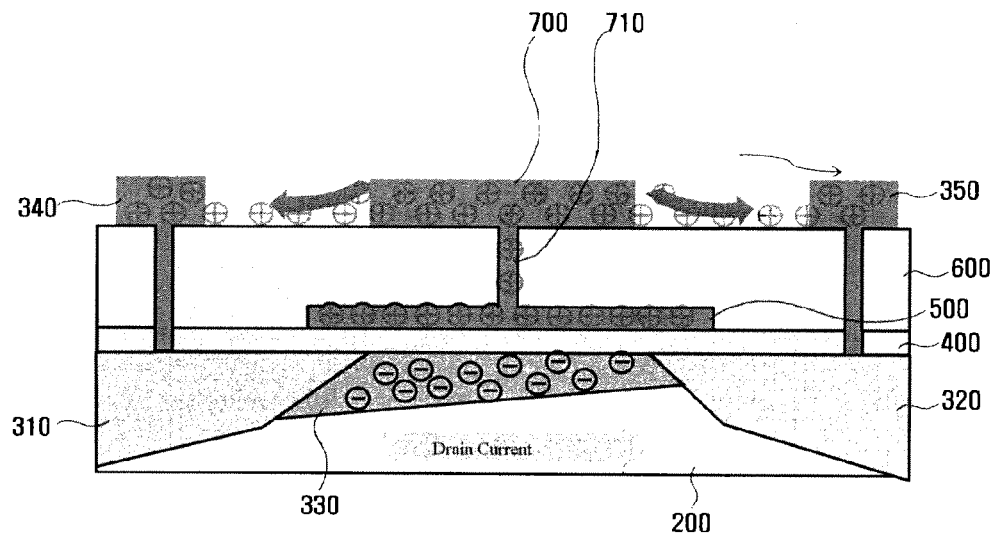
FIG. 2 shows an example of a transistor which can be used in the humidity sensor and the humidity sensing method according to an embodiment of the present invention.

FIG. 2 shows an example of a transistor which can be used in the humidity sensor and the humidity sensing method according to the embodiment of the present invention. FIG. 2 shows a structure designed for accurately measuring the humidity in accordance with the embodiment of the present invention. That is, the humidity sensor and the humidity sensing method according to the embodiment of the present invention may use a field effect transistor (FET).

The field effect transistor (FET) includes a gate 500, a source 310, and a drain 320.

The source 310 and the drain 320 are formed on a substrate 200 separately from each other with a channel area 330 placed therebetween. Also, the transistor according to the embodiment of the present invention may further include a hydrophobic layer 600 covering the gate 500, the source 310 and the drain 320, and the conductive material layer 700 which is connected to the gate 500 through a through-hole 710 formed in the hydrophobic layer 600 and is formed on the hydrophobic layer 600.

Here, the substrate 200 may be a silicon substrate and is not necessarily limited to this. When the substrate 200 is a silicon substrate, the substrate 200 may include any one of a general silicon substrate (bulk) and a silicon on insulator (SOI). The substrate 200 may be a p-type silicon substrate or an n-type silicon substrate depending on the kind of doped impurities.

The source 310 and the drain 320 are formed by doping an n-type impurity (group V element of the periodic table) or a p-type impurity (group III element of the periodic table) on the substrate 200. In addition, the transistor according to the embodiment of the present invention may further include a source electrode 340 connected to the source 310, and a drain electrode 350 connected to the drain 320.

On the substrate 200, the channel area 330 is defined between the source 310 and the drain 320. An insulation layer 400 is included on the channel area 330. While FIG. 2 shows the insulation layer 400 is formed on the source 310 and the drain 320, this is just an example and the insulation layer 400 can be formed only on the channel area 330. The insulation layer 400 may further include an insulation material such as silicon oxide or a high insulation material (High-K) between the gate 500 and the substrate 200. The gate 500 is located on the insulation layer 400 and includes a conductive material such as metal.

The hydrophobic layer 600 covers the gate 500, the source 310 and the drain 320. The hydrophobic layer 600 showing characteristics not combined with water molecules is able to protect the semiconductor from external pollutants and prevent water from directly contacting with the semiconductor. Therefore, it is possible to lubricate the transistor and/or the humidity sensor which is capable of stably operating. The hydrophobic layer 600 may further include, for example, silicon nitride.

The conductive material layer 700 connected to the gate 500 is formed on the hydrophobic layer 600. Here, the conductive material layer 700 may be connected to the gate 500 through the through-hole 710 formed in the hydrophobic layer 600.

The humidity sensor according to the embodiment of the present invention uses a principle in which a drain current of the transistor shown in FIG. 2 varies according to the change of the amount of the electric charge present at the gate. In other words, when a voltage is applied to the conductive material layer 700 or the gate 500 of the transistor, the drain current flows. The drain current flows through the channel area 330 shown in FIG. 2.

When the amount of the electric charge of the gate 500 is reduced, the drain current is hereby reduced. Here, a rate at which the electric charge of the gate 500 is reduced after the voltage application to the gate 500 is changed according to the humidity of the medium with which the hydrophobic layer 600 in contact with the conductive material layer 700 is in contact. This is because the electric charge applied to the gate 500 is not diffused through the surface of the insulation layer 400 and moves to the conductive material layer 700 through the through-hole 710, and then is discharged through the surface of the hydrophobic layer 600.

Therefore, after the voltage is applied to the gate 500 or the conductive material layer 700, the amount of the drain current change is measured for a certain period of time, thereby detecting the humidity of the medium in contact with the transistor, that is to say, the medium in contact with the hydrophobic layer 600.

Figure 3:
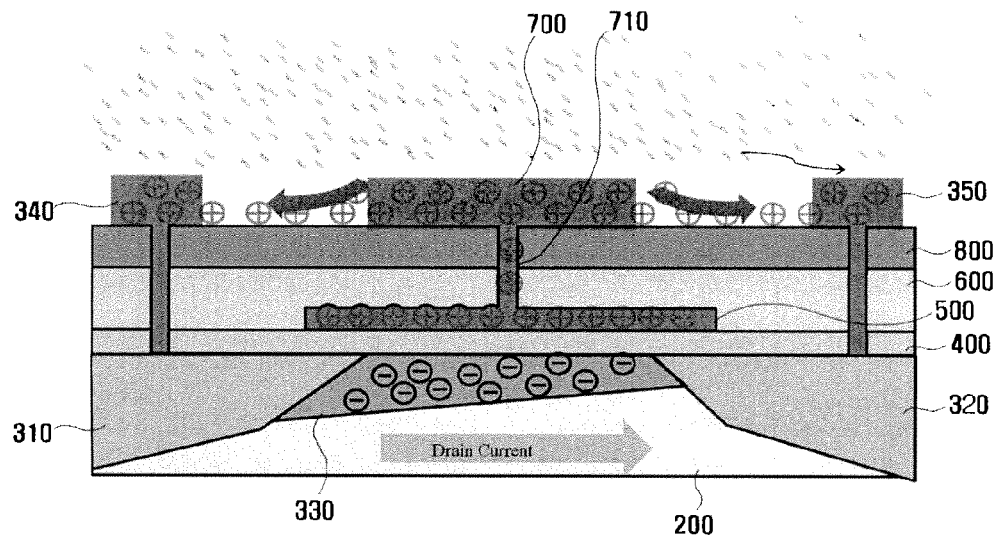
FIG. 3 shows another example of a transistor which can be used in the humidity sensor and the humidity sensing method according to the embodiment of the present invention.

FIG. 3 shows another example of a transistor which can be used in the humidity sensor and the humidity sensing method according to the embodiment of the present invention. The transistor of FIG. 3 is intended to rapidly and stably implement the humidity sensor.

A transistor according to another embodiment of the present invention is obtained by adding a humidity sensing layer 800 to the transistor shown in FIG. 2. The humidity sensing layer 800 is located between the hydrophobic layer 600 and the conductive material layer 700. The surface conductivity of the humidity sensing layer 800 changes with a wide range depending on the humidity.

The humidity sensing layer 800 is composed of, for example, silicon oxide ($SiO_2$), silicon nitride ($SiN_x$) or aluminum oxide ($Al_2O_3$). As described above, since the humidity sensing layer 800 of which the surface conductivity changes depending on the humidity is further included, the electric charges of the conductive material layer 700 or the gate 500 can be more rapidly discharged to the surface of the humidity sensing layer 800. Also, since the surface conductivity of the humidity sensing layer 800 changes with a wide range depending on the humidity, it is possible to more accurately measure the humidity around the transistor.

Here, a low capacitance device may be used as the insulation layer 400 or a surface resistance component of the humidity sensing layer 800 may be reduced in such a manner that the electric charges flow rapidly to the conductive material layer 700 through the through-hole 710 connected to the gate 500.

Also, in the transistor and the humidity sensor according to the embodiment of the present invention, if the hydrophobic layer 600 and/or the humidity sensing layer 800 are contaminated by hydrocarbon ($CH_4$), the surface resistance characteristics of them may be changed. Therefore, the transistor and the humidity sensor according to the embodiment of the present invention are able to remove the hydrocarbon by using a system capable of removing the hydrocarbon. Otherwise, the hydrophobic layer 600 and/or the humidity sensing layer 800 are manufactured such that hydrocarbon on the surfaces of the hydrophobic layer 600 and/or the humidity sensing layer 800 are saturated, so that the change of characteristics due to the hydrocarbon contamination can be prevented.

Since the operation principle of the humidity sensor using the transistor shown in FIG. 3 is the same as that of the humidity sensor using the transistor shown in FIG. 2, a description thereof will be omitted.

The humidity sensor according to the embodiment of the present invention may include a humidity sensing unit 920 shown in FIG. 1, 2 or 3, a charger 910 which charges the electric charges in the humidity sensing unit 920, and a measurer 930 which measures the change amount of the electric charges of the humidity sensing unit 920.

Figure 4:
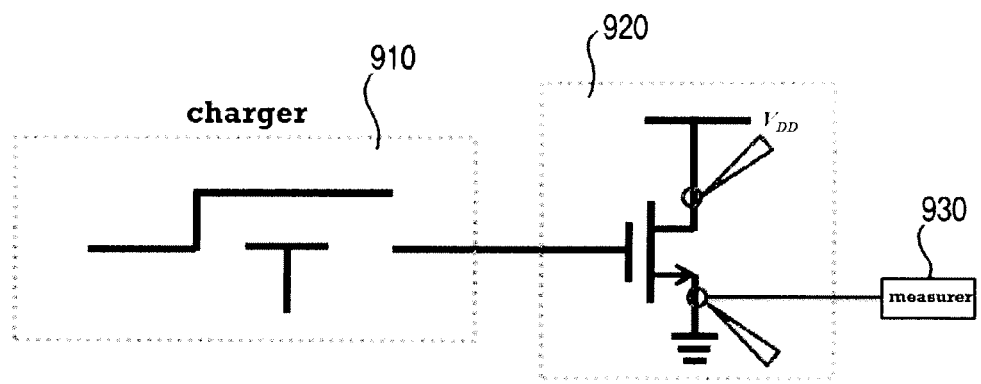
FIG. 4 shows a structure of the humidity sensor according to the embodiment of the present invention.

FIG. 4 shows an example of a structure of the humidity sensor according to the embodiment of the present invention. FIG. 4 shows that the transistor shown in FIG. 2 or 3 is used as the humidity sensing unit 920. FIG. 4 also shows that a micro-electro-mechanical system (MEMS) switch which applies a voltage to the gate 500 of the transistor is used as the charger 910 which charges the electric charges in the humidity sensing unit 920. This is only an example. The charger 910 may include any structure capable of applying the voltage to the gate 500 during a certain interval and stopping the voltage application.

The measurer 930 may be a current measurer which measures the amount of the drain current of the transistor.

Therefore, the humidity sensor according to the embodiment of the present invention shown in FIG. 4 applies a voltage to the gate 500 of the field effect transistor (FET) through the charger 910 during a certain time interval, and then stops the voltage application. Then, the drain current of the transistor is measured for a predetermined period of time, and the amount of the drain current change for the predetermined period of time from the applying of the voltage can be obtained. From this, the humidity of the medium with which the transistor has contacted can be calculated. Here, the gate 500 includes the conductive material layer 700 connected to the gate 500.

Figure 5:
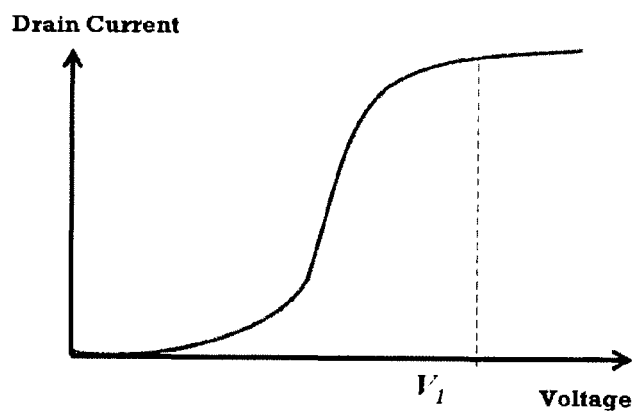
FIG. 5 shows a correlation between a voltage and a drain current which are applied to the transistor used in the humidity sensor according to the embodiment of the present invention.

FIG. 5 shows a correlation between a voltage and a drain current which are applied to the transistor used in the humidity sensor according to the embodiment of the present invention. As shown in FIG. 5, it can be seen that the drain current varies depending on the magnitude of the voltage applied to the gate 500.

Therefore, the charger 910 of FIG. 4 may apply a voltage "Vt" to the gate 500 of the transistor and stop the voltage application.

Figure 6:
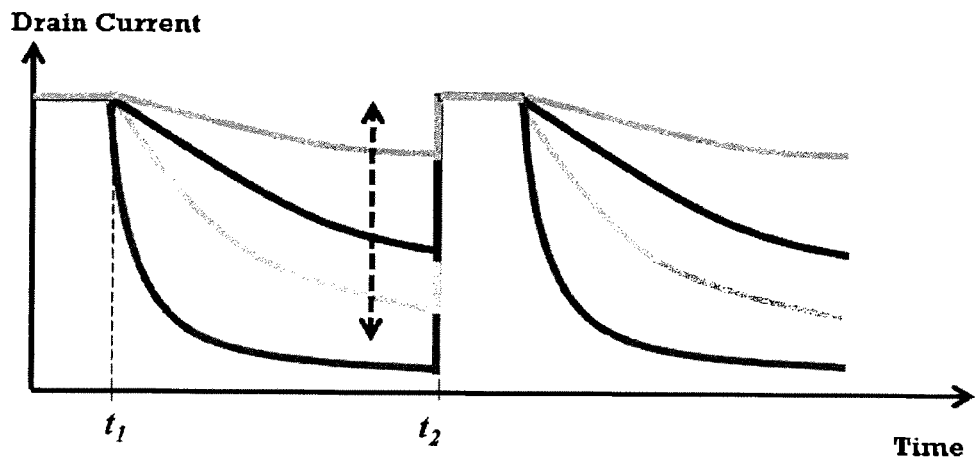
FIG. 6 shows the change depending on time of the drain current of the transistor used in the humidity sensor according to the embodiment of the present invention.

FIG. 6 shows the change depending on time of the drain current of the transistor used in the humidity sensor according to the embodiment of the present invention. As shown in FIG. 6, it can be seen that the drain current is constant until a first period of time "t1" during which the voltage is applied. After the first period of time "t1", the voltage application by the charger 910 is stopped.

During a time during which the voltage is not applied, that is, after the first time "t1" to a second time "t2", the electric charges present at the gate 500 are diffused into the surface of the material in contact with the conductive material layer 700, for example, the hydrophobic layer 600 or the humidity sensing layer 800. As a result, the drain current of the transistor is reduced. This is shown in FIG. 6. Here, the reduction amount of the drain current is changed depending on the humidity of the medium with which the transistor has contacted.

Accordingly, after the voltage application, the amount of the drain current change is measured for the predetermined period of time (after the first time "t1" to the second time "t2"), so that the humidity of the medium with which the transistor has contacted can be determined.

The humidity measurement process can be continuously repeated. This shows the current change shown in FIG. 6.

Figure 7:
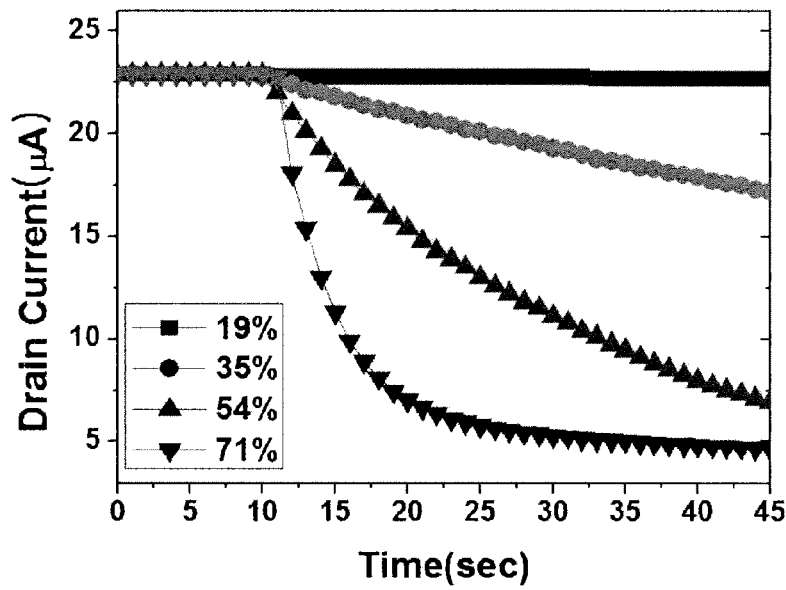
FIG. 7 is a graph showing a result of measuring the drain current of the transistor shown in FIG. 3 in accordance with the lapse of time under different humidity conditions.

FIG. 7 is a graph showing a result of measuring the drain current of the transistor shown in FIG. 3 in accordance with the lapse of time under different humidity conditions.

As shown in FIG. 7, the charging of the electric charges to the transistor is stopped at a time point of 11 sec. Then, the drain current follows mutually different change curves in accordance with the humidity of the medium at which the transistor is located. It can be found that the change range and change rate of the drain current is increased with the increase of the humidity.

Further, it is noteworthy that the drain current is rapidly reduced within 2 to 3 seconds after the voltage application is stopped. Considering the conventional humidity sensor using a humidity sensing film requires tens of seconds, it can be understood that the reduction rate of the drain current of the humidity sensor according to the present invention is very high.

As described above, it is possible to rapidly and accurately measure the humidity of the medium in contact with the transistor by measuring the reduction amount of the drain current of the transistor after charging of the electric charges.

Figure 8:
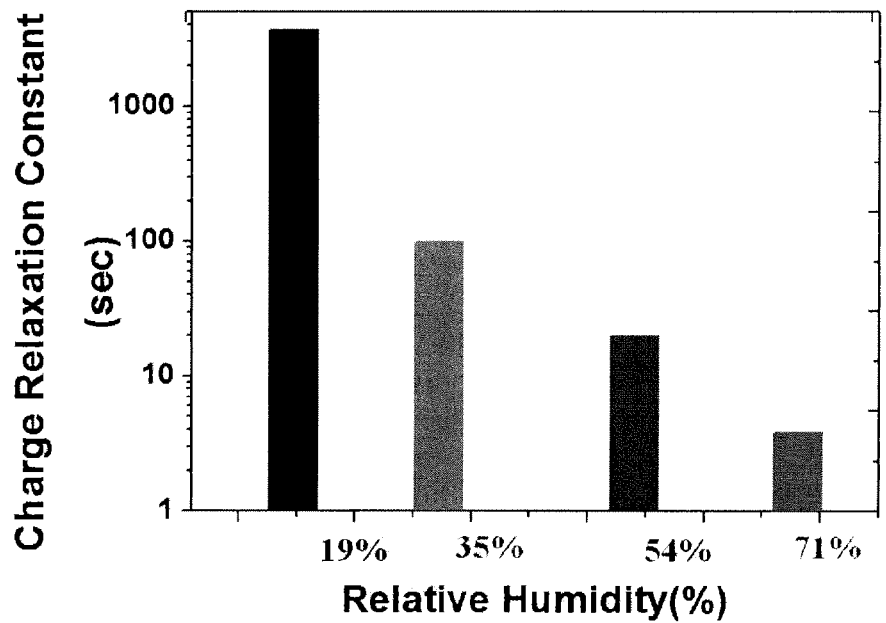
FIG. 8 shows that an electric charge relaxation constant of a humidity sensing layer used in the transistor according to the embodiment of the present invention is changed according to a relative humidity.

FIG. 8 shows that the electric charge relaxation constant of a humidity sensing layer used in the transistor according to the embodiment of the present invention is changed according to a relative humidity. As shown in FIG. 8, it is to be understood that the change amount of the charge relaxation constant (RsCs) of the humidity sensing layer 800 is very large depending on the change of the relative humidity. Depending on the change of the humidity, there is an approximate 970-fold difference between the change amounts of the charge relaxation constant of the humidity sensor including the humidity sensing layer 800 according to the embodiment of the present invention. Accordingly, the humidity can be very precisely measured by using the transistor or the humidity sensor according to the embodiment of the present invention.

Figure 9:
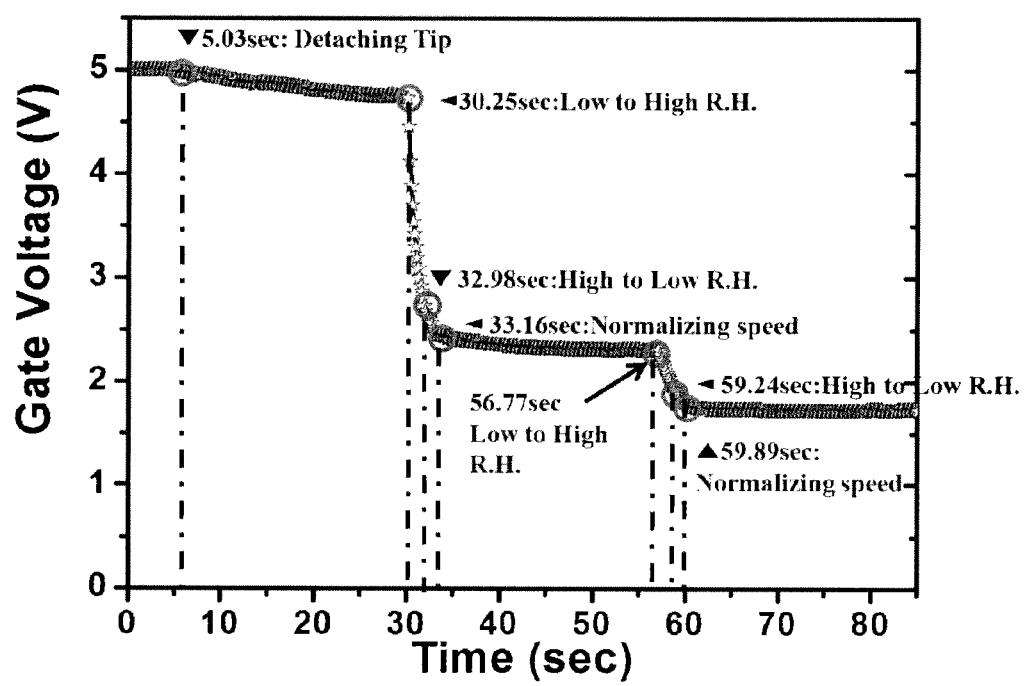
FIG. 9 is a graph showing a result of measuring a reaction rate of the humidity sensor according to the embodiment of the present invention.

FIG. 9 is a graph showing a result of measuring a reaction rate of the humidity sensor according to the embodiment of the present invention. In FIG. 9, the electric charge application to the gate 500 of the transistor is stopped in the vicinity of a time point of 5.03 sec. Here, since the transistor is located in a low humidity medium in a time interval of from 5.03 sec. to 30.25 sec., the slope of the gate voltage reduction is very small. The aforementioned transistor moves to a high humidity medium at a time point of 30.25 sec., and then it can be found that the electric charges of the gate begin to discharge at a very high speed.

Then, the humidity sensor moves again to the low humidity medium at a time point of 32.98 sec. and it can be seen that the gate voltage is reduced from a time point of 33.16 sec., at a speed in accordance with the low humidity. In other words, it can be seen that the humidity sensor according to the embodiment of the present invention resumes a humidity sensing speed within 1 second. That is, it can be seen that the humidity sensor according to the embodiment of the present invention has a very short recovery time for reaching a state of measuring the humidity again after measuring the humidity. This process is repeated one more time in FIG. 9. A similar recovery time can be seen in a time interval of from 59.24 sec. to 59.89 sec. in FIG. 9.

As described above, since the present invention makes use of the surface reaction instead of a film which should absorb the moisture, it is possible to implement the humidity sensor having a high reaction rate and a high recovery rate. Also, the humidity sensor according to the embodiment of the present invention does not use the humidity sensing film. Therefore, it is possible to stably sense the humidity even under high temperature and high humidity conditions. In addition, it is also possible to implement the humidity sensor which reliably operates for a long time.

Also, in the humidity sensor and the humidity sensing method according to the present invention, as long as the surface resistance change occurs, it is possible to detect the humidity in any environment and in any medium. For example, when polar molecules are present in the atmosphere, the conductivity of the surface is changed. Accordingly, ammonia and other polar molecular substance can be detected.

When the humidity sensor according to the present invention uses the transistor, the entire sensor manufacturing process consists of the semiconductor process. Therefore, the humidity sensor can be smaller and mass-produced. As a result, high reliability and high reproductivity can be obtained at a low cost. Also, the humidity sensor is integrated with other semiconductor devices on one substrate, so that it is possible to detect the humidity on a circuit board.

Also, according to the present invention, the micro-electro-mechanical system (MEMS) switch is used as the charger, so that it is possible to accurately apply the voltage to the transistor for a short time and to rapidly and accurately detect the humidity.

While the embodiment of the present invention has been described with reference to the accompanying drawings, it can be understood by those skilled in the art that the present invention can be embodied in other specific forms without departing from its spirit or essential characteristics. Therefore, the foregoing embodiments and advantages are merely exemplary and are not to be construed as limiting the present invention. The present teaching can be readily applied to other types of apparatuses. The description of the foregoing embodiments is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

INDUSTRIAL APPLICABILITY

In the humidity sensor and the humidity sensing method according to the present invention, as long as the surface resistance change occurs, it is possible to detect the humidity in any environment and in any medium. For example, when polar molecules are present in the atmosphere, the conductivity of the surface is changed. Accordingly, ammonia and other polar molecular substance can be detected.

The invention claimed is:
1. A humidity sensor comprising:
    a transistor including a source and a drain which are formed on a substrate separately from each other with a channel area placed therebetween,
    an insulation layer formed on the channel area,
    a gate formed on the insulation layer,
    a hydrophobic layer covering the gate, the source and the drain, and
    a conductive material layer which is connected to the gate through a through-hole formed in the hydrophobic layer and is formed on the hydrophobic layer;
    a charger which charges electric charges in the gate; and
    a measurer measuring a change amount of drain current of the transistor during a predetermined time period after stopping the charging of the electric charges in the gate,
    wherein humidity of a medium in contact with the gate is calculated based on the measured change amount of the drain current.
2. The humidity sensor of claim 1, wherein the charger is a micro-electro-mechanical system (MEMS) switch.
3. The humidity sensor of claim 1, wherein the hydrophobic layer comprises a silicon nitride film.
4. The humidity sensor of claim 3, wherein the conductive material layer comprises metal.
5. The humidity sensor of claim 1, further comprising a humidity sensing layer which is located between the hydrophobic layer and the conductive material layer and of which surface conductivity changes depending on the humidity.
6. The humidity sensor of claim 5, wherein the humidity sensing layer comprises silicon oxide ($SiO_2$), silicon nitride (SiNx) or aluminum oxide ($Al_2O_3$).
7. A humidity sensing method comprising:
    charging electric charges in a gate of a transistor, wherein the transistor includes
        a source and a drain which are formed on a substrate separately from each other with a channel area placed therebetween,
        an insulation layer formed on the channel area,
        the gate formed on the insulation layer,
        a hydrophobic layer covering the gate, the source and the drain, and
        a conductive material layer which is connected to the gate through a through-hole formed in the hydrophobic layer and is formed on the hydrophobic layer;
    measuring a change amount of drain current of the transistor during a predetermined time period after stopping the charging of the electric charges in the gate; and
    calculating humidity of a medium in contact with the gate based on the measured change amount of the drain current.
8. The humidity sensing method of claim 7, wherein the charging the electric charges in the gate is performed by a micro-electro-mechanical system (MEMS) switch.
9. The humidity sensing method of claim 7, wherein the transistor further comprises a humidity sensing layer which is located between the hydrophobic layer and the conductive material layer and of which surface conductivity changes depending on the humidity.

* * * * *